(12) United States Patent
Chen

(10) Patent No.: US 10,702,417 B2
(45) Date of Patent: Jul. 7, 2020

(54) SNOW GOGGLE STRUCTURE HAVING STRAP

(71) Applicant: PROHERO GROUP CO., LTD., Tainan (TW)

(72) Inventor: Pen-Wei Chen, Tainan (TW)

(73) Assignee: Prohero Group Co., Ltd., Tainan (TW)

( * ) Notice: Subject to any disclaimer, the term of this patent is extended or adjusted under 35 U.S.C. 154(b) by 78 days.

(21) Appl. No.: 16/003,298

(22) Filed: Jun. 8, 2018

(65) Prior Publication Data
US 2019/0374385 A1 Dec. 12, 2019

(51) Int. Cl.
*A61F 9/02* (2006.01)
*A63B 33/00* (2006.01)

(52) U.S. Cl.
CPC .............. *A61F 9/027* (2013.01); *A63B 33/00* (2013.01); *A63B 33/002* (2013.01)

(58) Field of Classification Search
CPC ........ A61F 9/027; A63B 33/00; A63B 33/002
See application file for complete search history.

(56) References Cited

U.S. PATENT DOCUMENTS

| | | | | |
|---|---|---|---|---|
| 2,903,700 A * | 9/1959 | Finken | ..................... | A61F 9/025 2/10 |
| 4,649,577 A * | 3/1987 | Wiedner | ................. | A61F 9/028 2/436 |
| 6,715,157 B2 * | 4/2004 | Mage | ...................... | A61F 9/027 2/426 |
| 2008/0204653 A1 * | 8/2008 | Fielding | ................. | G02C 3/003 351/156 |
| 2014/0250573 A1 * | 9/2014 | Mcneal | .................... | A61F 9/027 2/436 |
| 2015/0128385 A1 * | 5/2015 | Kuo | ...................... | A44B 11/006 24/193 |
| 2019/0192347 A1 * | 6/2019 | Prugue | .................... | A61F 9/027 |

* cited by examiner

*Primary Examiner* — Khaled Annis
(74) *Attorney, Agent, or Firm* — Rosenberg, Klein & Lee

(57) ABSTRACT

A snow goggle structure having a strap is disclosed herein. It comprises a main body having two securing holes on two sides thereof, two fixed stands assembled to the two securing holes and each having an assembly hole, two connecting elements each having a connecting rod, an assembly part for inserting into the assembly hole of each of the two fixed stands, and an active casing; and two moving elements each having a slot, an axial part in the slot for pivotally connecting the active casing connected to the connecting rod, and a connecting part on a side surface thereof for connecting one end of a strap for fixation.

6 Claims, 6 Drawing Sheets

US 10,702,417 B2

SNOW GOGGLE STRUCTURE HAVING STRAP

BACKGROUND OF THE INVENTION

1. Field of the Invention

The present invention relates to provide a snow goggle structure having a strap which has different patterns on its front and back sides and can be easily and arbitrarily flipped to the front or back side for use so as to increase overall appearance and practicality of overall implementation.

2. Description of Related Art

When riding a motorcycle or a bicycle, or skiing in the snow, people usually wear a snow goggle to prevent the eyes from being affected or damaged by wind, snow, or other intrusive objects. Generally, a snow goggle comprises a frame which is designed according to the curve of the human face and can completely cover the user's eyes and around the eyes, a lens assembly hole disposed at an anterior of the frame, a concave groove at a periphery of the lens assembly hole for assembling and positioning lenses, a plurality of ventilation hole disposed on a top face and a bottom face of the frame and parallel to each other, and two perforations respectively disposed on two sides of the frame for connecting and fixing two ends of a strap. Accordingly, the snow goggle can cover the user's eyes and the space around the eyes, and the transparent lenses prevents objects, e.g. the wind, snow and foreign objects, from hitting the eye, which allow the user to clearly see the surrounding environment when wearing the snow goggle.

Although the abovementioned snow goggle achieves various expected efficacy, e.g. protecting the eyes from intrusive objects and clearly seeing the environment, it has some restrictions on the overall structural design that need to be improved. For instance, the strap of the snow goggle can't be flipped freely because it is pierced directly on the two sides of the frame, so the strap can be used only on one surface which is a bit monotonous in its overall design.

SUMMARY OF THE INVENTION

In view of the above-mentioned problems, the object of the present invention is to provide a snow goggle structure having a strap which has different patterns on its front and back sides and can be easily and arbitrarily flipped to the front or back side for use so as to increase overall appearance and practicality of overall implementation.

Disclosed herein is a snow goggle structure having a strap. It comprises a main body, two fixed stands, two connecting elements, and two moving elements.

The main body is provided with two securing holes on two sides thereof.

The two fixed stands are assembled to the two securing holes of the main body and each of the two fixed stands is provided with an assembly hole.

Each of the two connecting elements is provided with a connecting rod, an assembly part connected to one end of the connecting rod for inserting into the assembly hole, and an active casing pivotally connected to the other end of the connecting rod.

Each of the two moving elements is provided with a slot corresponding to the active casing of each of the two connecting elements, an axial part in the slot for pivotally connecting the active casing, and a connecting part on a side surface thereof for connecting one end of a strap for fixation.

According to an embodiment of the present invention, the assembly hole of each of the two fixed stands is shaped as an ellipse, and the assembly part of each of the two connecting elements is also shaped as an ellipse so that the assembly part can be horizontally inserted into the assembly hole and then rotated to be perpendicular to the assembly hole for connection and fixation.

DETAILED DESCRIPTION OF THE PREFERRED EMBODIMENT

Hereinafter, an exemplary embodiment of the present invention will be described in detail with reference to the accompanying drawings.

Figure 1:
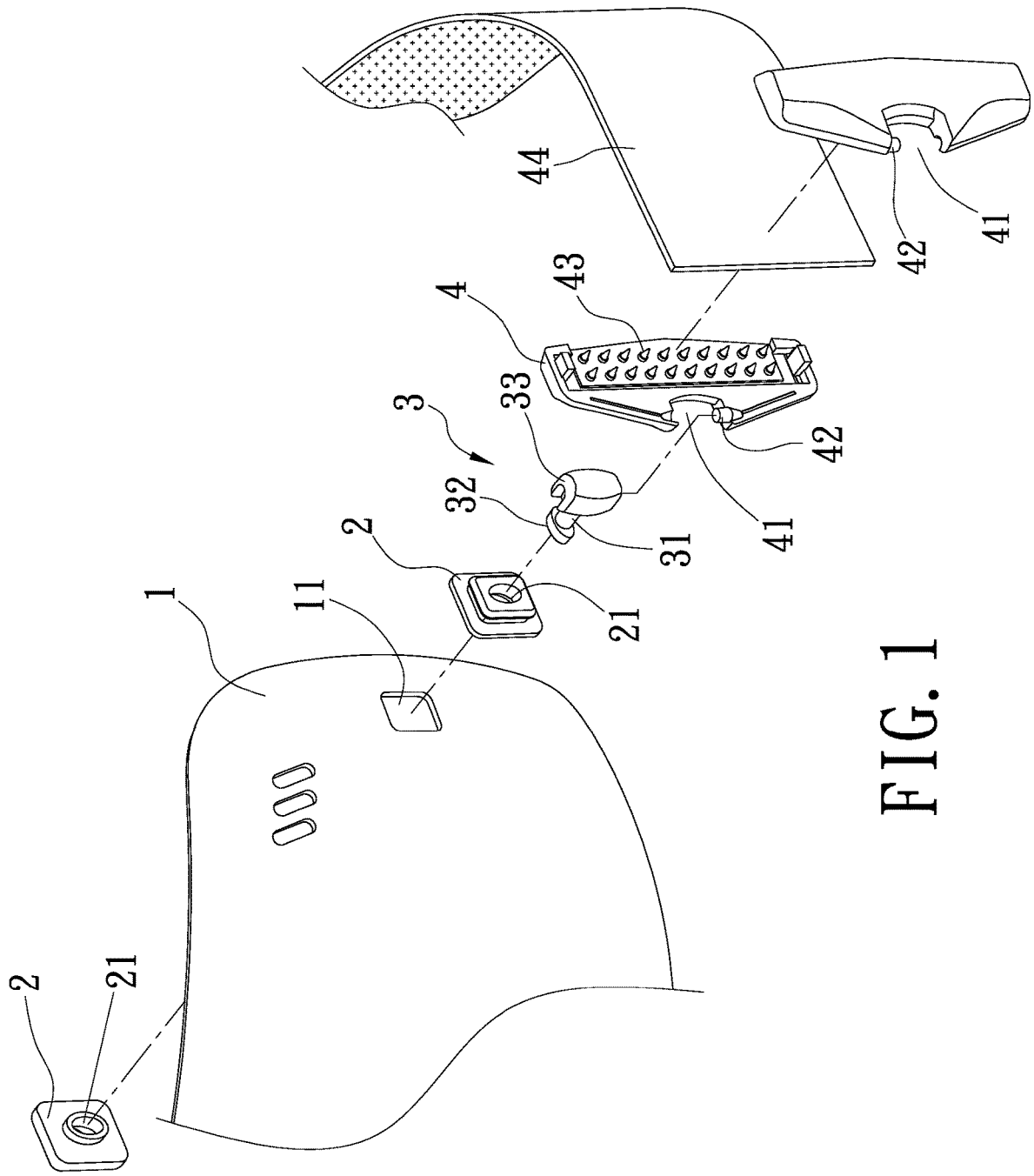
FIG. 1 is an explosion diagram showing a snow goggle structure having a strap according to the present invention.

As showed in FIG. 1, an explosion diagram showing a snow goggle structure having a strap according to the present invention is disclosed. The snow goggle structure having a strap mainly comprises a main body (1), two fixed stands (2), two connecting elements (3) and two moving elements (4).

The main body (1) is provided with two securing holes (11) on its two sides.

The two fixed stands (2) are assembled to the two securing holes (11) of the main body (1) and each of the two fixed stands (2) is provided with an assembly hole (21) shaped as an ellipse.

Each of the two connecting elements (3) is provided with a connecting rod (31), an assembly part (32) connected to one end of the connecting rod (31) and also shaped as an ellipse for correspondingly inserting into the assembly hole (21), and an active casing (33) pivotally connected to the other end of the connecting rod (31).

Each of the two moving elements (4) is provided with a slot (41) corresponding to the active casing (33) of each of the two connecting elements (3), an axial part (42) in the slot (41), and a connecting part (43) on its side surface for connecting one end of a strap (44) for fixation.

Figure 2:
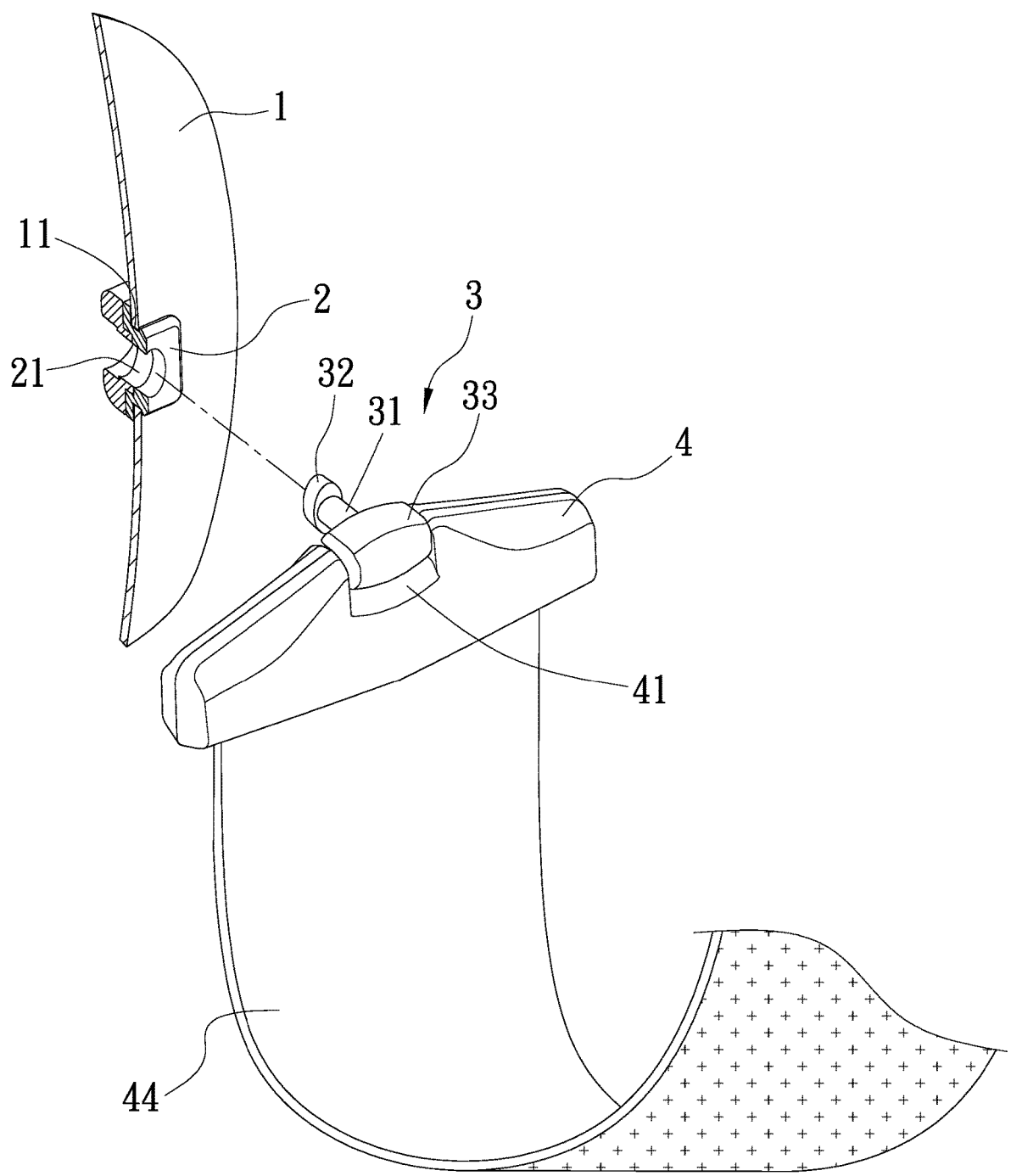
FIG. 2 is a partial explosion diagram showing a snow goggle structure having a strap according to the present invention.
Figure 3:
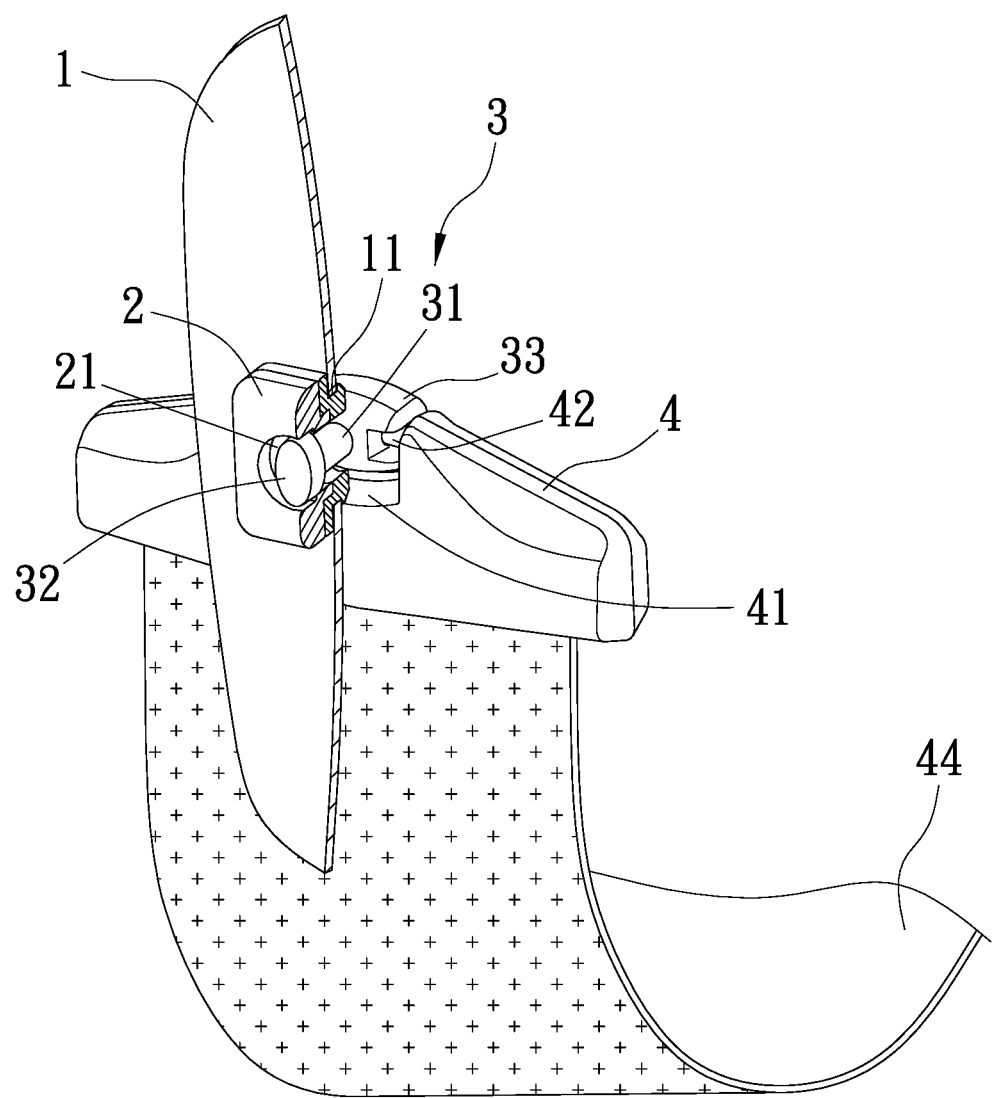
FIG. 3 is a cross-sectional view showing a snow goggle structure having a strap in assembly according to the present invention.
Figure 4:
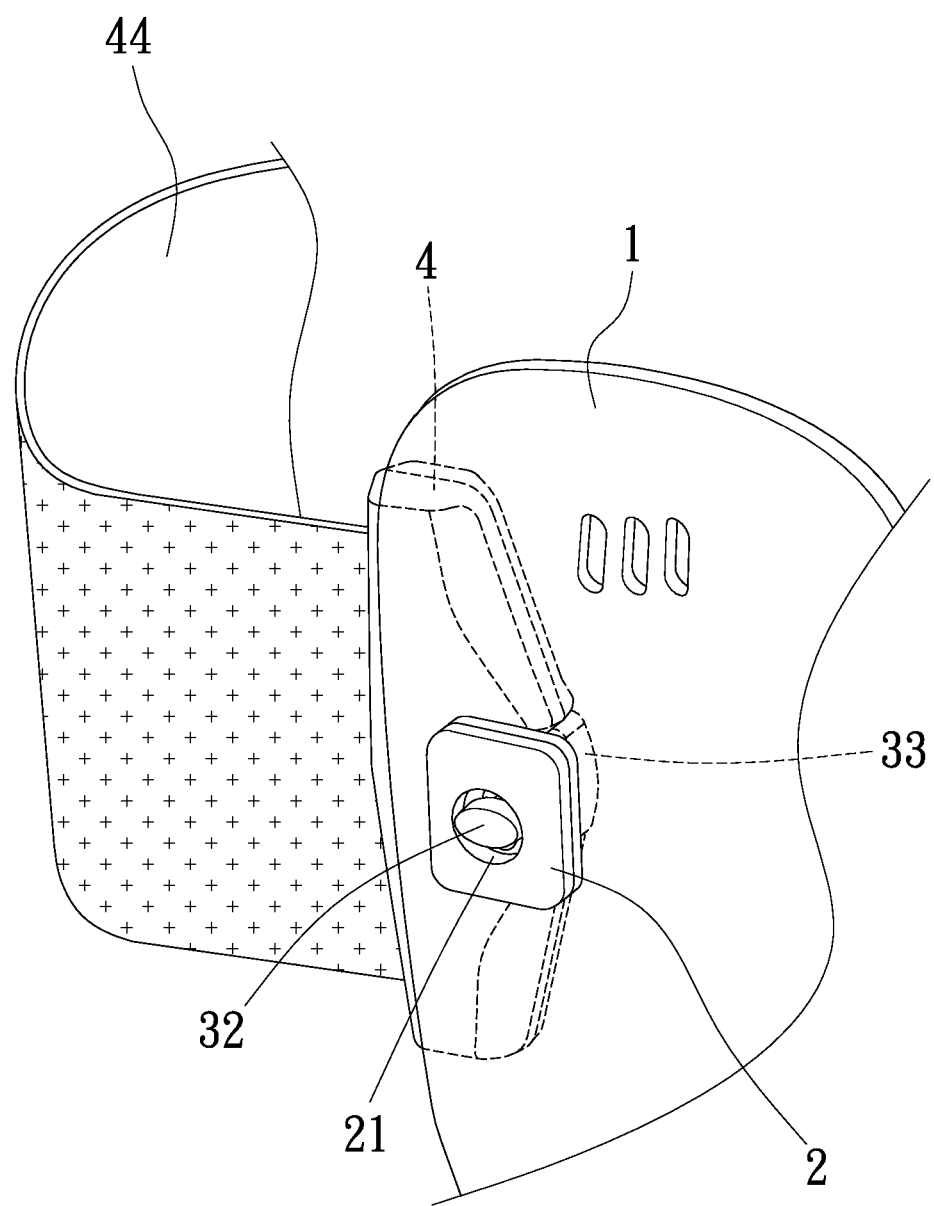
FIG. 4 is a partial perspective view showing a snow goggle structure having a strap in assembly according to the present invention.
Figure 5:
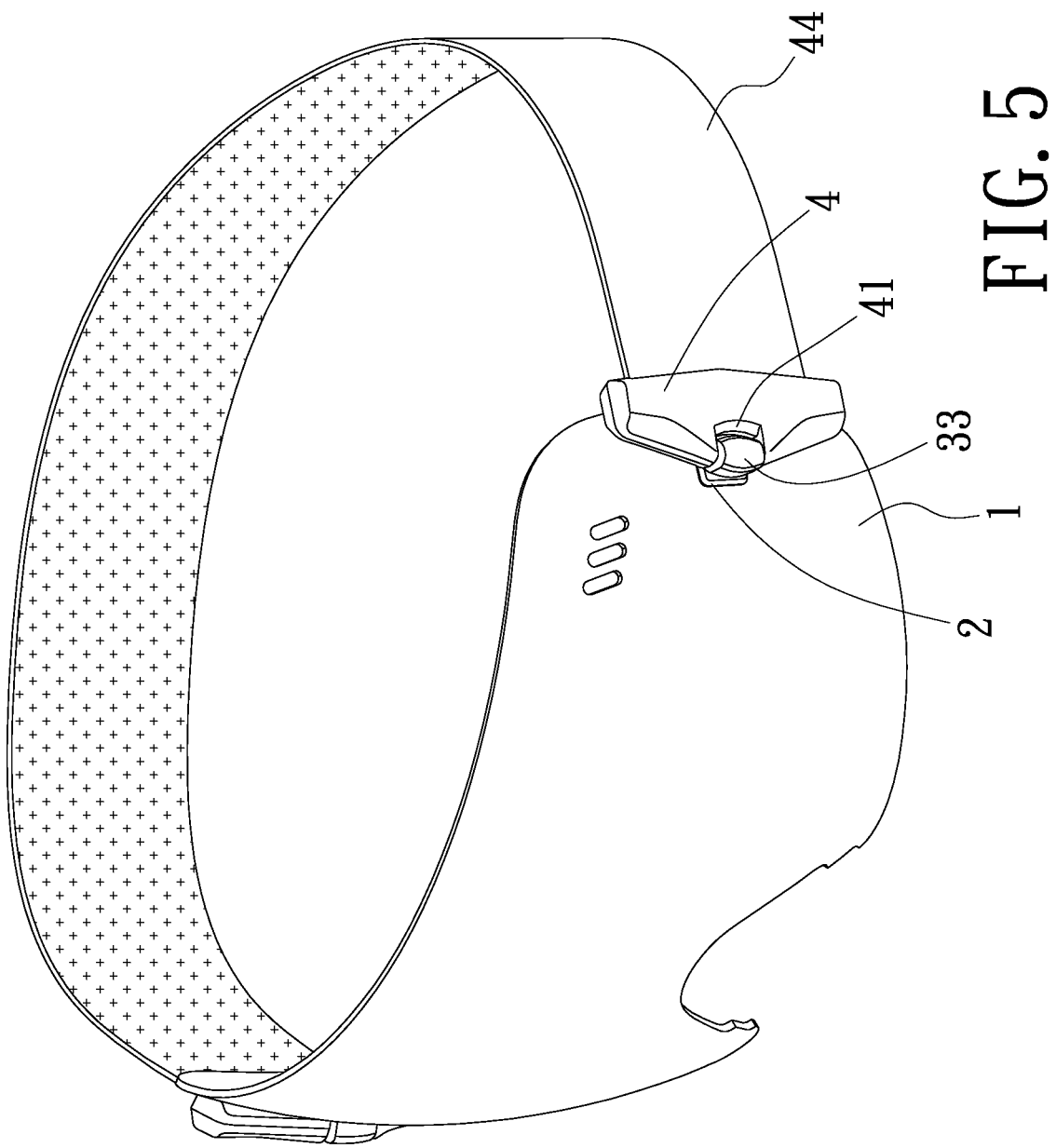
FIG. 5 is a stereogram for a first embodiment showing a snow goggle structure having a strap in assembly according to the present invention.

Referring to FIG. 2 to FIG. 4, a partial explosion diagram, a cross-sectional view, and a partial perspective view showing a snow goggle structure having a strap in assembly according to the present invention are respectively revealed. Each of the two fixed stands (2) is assembled to each of the two securing holes (11) of the main body (1), and the moving elements (4) is fixed by the connecting part (43) connecting the strap (44). The active casing (33) of each of the two connecting elements (3) is correspondingly accommodated in the slot (41) of each of the two moving elements (4). The axial part (42) in the slot (41) is pivotally connected to the active casing (33), and then the assembly part (32) of each of the two connecting elements (3) is correspondingly inserted into the assembly hole (21) of each of the two fixed stands (2). If the assembly hole (21) and the assembly part (32) are all shaped as an ellipse corresponding to each other, the assembly part (32) can be horizontally inserted into the assembly hole (21) and rotated to be perpendicular to the assembly hole (21) for fixation as shown in FIG. 5.

Figure 6:
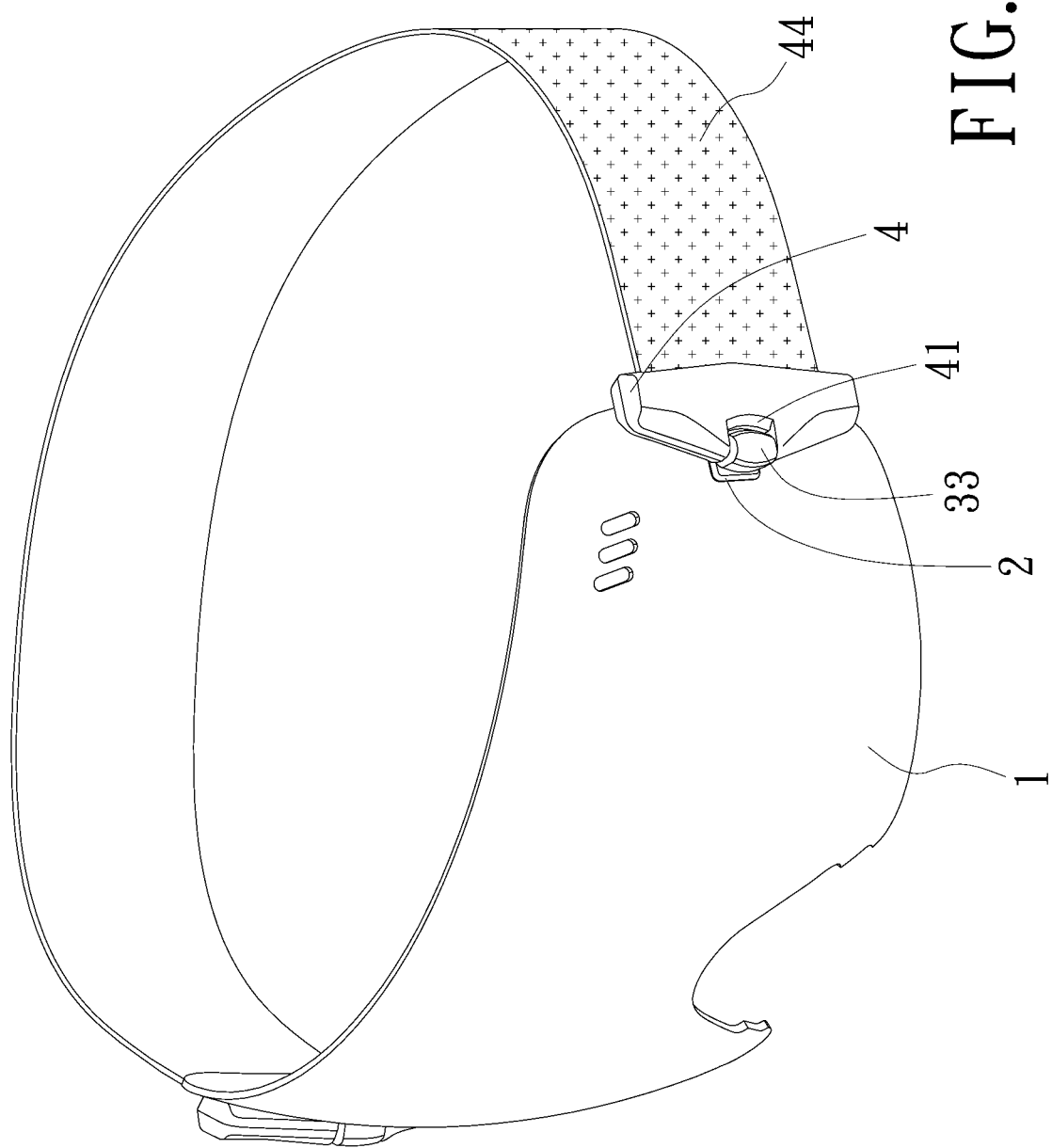
FIG. 6 is a stereogram for a second embodiment showing a snow goggle structure having a strap in assembly according to the present invention.

Referring to FIG. 6, when a user wants to flip the strap (44) to use the other surface of the strap (44), each of the two moving elements (4) is driven to rotate forwards on the active casing (33) of each of the two connecting elements (3) and then turned backwards on the axial part (which can be a shaft portion) (42) pivotally connected to the active casing (which can be a movable sleeve) (33) so that one end of the strap (44) fixed on the connecting part (43) of each of the two moving elements (4) is flipped to the other surface for use.

According to the above description, in comparison with the traditional technique, the snow goggle structure having a strap according to the present invention has the advantages of having different patterns on its front and back sides and being easily and arbitrarily flipped to the front or back side for use. Therefore, the present invention improves appearance and increases practicality of overall implementation.

What is claimed is:

1. A snow goggle structure having a strap, comprising:
   a main body having two securing holes on two sides thereof;
   two fixed stands inserted in the two securing holes of the main body and each having an assembly hole;
   two connecting elements, each having:
     a connecting rod,
     an assembly part connected to one end of the connecting rod and configured for passage through the assembly hole of each of the two fixed stands, and
     an active casing pivotally connected to an other end of the connecting rod; and
   two moving elements, each having:
     a slot,
     an axial part disposed in the slot and pivotally connected to the active casing of one of the two connecting elements, and
     a connecting part formed on a side surface of the moving element for connecting with one end of the strap for fixation.

2. The snow goggle structure having a strap as claimed in claim 1, wherein the assembly hole of each of the two fixed stands is shaped as an ellipse, and wherein the assembly part of each of the two connecting elements is shaped as an ellipse for horizontally inserting into the assembly hole and rotating to be perpendicular to the assembly hole for fixation of the connecting element relative to the fixed stand.

3. The snow goggle structure having a strap as claimed in claim 1, wherein each active casing is pivotally connected to the corresponding connecting rod on a first axis, and each axial part is pivotally connected to the corresponding active casing on a second axis, each second axis oriented at a different angle than the corresponding first axis.

4. A connecting structure for connecting a snow goggle main body to an end of a strap, comprising:
   a fixed stand for inserting in a securing hole of the snow goggle main body, the fixed stand including an assembly hole;
   a connecting element including:
     a connecting rod,
     an assembly part connected to one end of the connecting rod and configured for passage through the assembly hole of the fixed stand, and
     an active casing connected to an other end of the connecting rod; and
   a moving element including:
     a slot,
     an axial part disposed in the slot and pivotally connected to the active casing of the connecting element, and
     a connecting part formed on a side surface of the moving element for connecting with one end of the strap for fixation.

5. The connecting structure as claimed in claim 4, wherein the assembly hole of the fixed stand is shaped as an ellipse, and wherein the assembly part of the connecting element is shaped as an ellipse for horizontally inserting into the assembly hole and rotating to be perpendicular to the assembly hole for fixation of the connecting element relative to the fixed stand.

6. The connecting structure as claimed in claim 4, wherein the connecting rod is pivotally connected to the assembly hole on a first axis, and the axial part is pivotally connected to the active casing on a second axis oriented at a different angle than the first axis.

* * * * *